United States Patent
Alvarez et al.

(10) Patent No.: US 11,285,035 B2
(45) Date of Patent: Mar. 29, 2022

(54) SINGLE ARCH DENTAL DEVICE AND METHOD OF MANUFACTURE

(71) Applicant: Dental Choice Holdings LLC, Louisville, KY (US)

(72) Inventors: Ramiro Michael Alvarez, Fremont, CA (US); Jose Sergio Alvarez, Fremont, CA (US)

(73) Assignee: Dental Choice Holdings LLC, Louisville, KY (US)

( * ) Notice: Subject to any disclaimer, the term of this patent is extended or adjusted under 35 U.S.C. 154(b) by 123 days.

(21) Appl. No.: 16/516,958

(22) Filed: Jul. 19, 2019

(65) Prior Publication Data
US 2021/0015657 A1 Jan. 21, 2021

(51) Int. Cl.
| A61F 5/56 | (2006.01) |
| A61C 7/36 | (2006.01) |
| A61B 5/00 | (2006.01) |
| A61C 7/08 | (2006.01) |

(52) U.S. Cl.
CPC ............. *A61F 5/566* (2013.01); *A61C 7/36* (2013.01); *A61B 5/4806* (2013.01); *A61C 7/08* (2013.01); *A61F 2005/563* (2013.01)

(58) Field of Classification Search
CPC ...... A61F 5/56; A61F 5/566; A61F 2005/563; A61C 7/08; A61C 7/36; A61C 7/10; A61C 17/0211; A61C 19/063; A61C 19/066; A61C 9/0006; A61C 5/90; A63B 1/085;
(Continued)

(56) References Cited

U.S. PATENT DOCUMENTS

| 2,659,366 A | 11/1953 | Savarese |
| 3,124,129 A | 3/1964 | Grossberg |
| 3,496,936 A | 2/1970 | Gores |

(Continued)

FOREIGN PATENT DOCUMENTS

| CA | 2668913 A1 | 5/2008 |
| DE | 29509294 | 5/1995 |

(Continued)

OTHER PUBLICATIONS

Moses D.D.S., Allen J.; Evolution of Theory on Oral Appliances and Exercises for Sleep Apnea and Snoring; Sleep Diagnosis and Therapy, vol. 5 No. 7, Nov.-Dec. 2010.

(Continued)

*Primary Examiner* — Camtu T Nguyen
(74) *Attorney, Agent, or Firm* — Middleton Reutlinger

(57) ABSTRACT

A single arch dental device. The single arch dental device includes a dental trough, having a lingual surface, a facial surface, and an occlusal surface. The dental trough is molded to conform to a shape of a wearer's lower teeth. The facial surface of the dental trough has an anterior facial surface and a posterior facial surface. The posterior facial surface of the dental trough is contoured to receive a facial surface of the wearer's teeth. The lingual surface of the dental trough has an anterior lingual surface and a posterior lingual surface. The anterior lingual surface of the dental trough is contoured to receive the lingual surface of the wearer's teeth. A pocket is carved out of the posterior lingual surface of the dental trough and provides a surface into which an anterior and lateral border portion of the wearer's tongue rests.

9 Claims, 8 Drawing Sheets

(58) Field of Classification Search
CPC ........ A63B 2071/086; A63B 2071/088; A63B 13/00
See application file for complete search history.

(56) References Cited

U.S. PATENT DOCUMENTS

| | | | |
|---|---|---|---|
| 3,924,638 | A | 12/1975 | Mann |
| 4,519,386 | A | 5/1985 | Sullivan |
| 4,955,393 | A | 9/1990 | Adell |
| 5,052,409 | A | 10/1991 | Tepper |
| 5,194,003 | A | 3/1993 | Garay et al. |
| 5,316,020 | A | 5/1994 | Truffer |
| 5,406,963 | A | 4/1995 | Adell |
| 5,536,168 | A | 7/1996 | Bourke |
| 5,584,687 | A | 12/1996 | Sullivan |
| 5,718,575 | A | 2/1998 | Cross, III |
| 5,752,822 | A | 5/1998 | Robson |
| 5,865,619 | A | 2/1999 | Cross, III et al. |
| 6,012,919 | A | 1/2000 | Cross, III et al. |
| 6,092,524 | A | 7/2000 | Barnes |
| 6,237,601 | B1 | 5/2001 | Kittelsen et al. |
| 6,241,518 | B1 | 6/2001 | Sullivan |
| 6,257,239 | B1 | 7/2001 | Kittelsen et al. |
| 6,371,758 | B1 | 4/2002 | Kittlesen |
| 6,415,794 | B1 | 7/2002 | Kittelsen et al. |
| 6,467,484 | B1 | 10/2002 | De Voss |
| 6,491,036 | B2 | 12/2002 | Cook |
| 6,505,626 | B2 | 1/2003 | Kittelsen et al. |
| 6,505,627 | B2 | 1/2003 | Kittelsen et al. |
| 6,505,628 | B2 | 1/2003 | Kittelsen et al. |
| 6,508,251 | B2 | 1/2003 | Kittelsen et al. |
| 6,510,853 | B1 | 1/2003 | Kittelsen et al. |
| 6,533,943 | B1 | 4/2003 | Kittelsen et al. |
| 6,553,996 | B2 | 4/2003 | Kittelsen et al. |
| 6,581,604 | B2 | 6/2003 | Cook |
| 6,588,430 | B2 | 7/2003 | Kittelsen et al. |
| 6,598,365 | B2 | 7/2003 | Abraham et al. |
| 6,598,605 | B1 | 7/2003 | Kittlesen et al. |
| 6,626,180 | B1 | 9/2003 | Kittelsen |
| 6,675,806 | B2 | 1/2004 | Kittelsen et al. |
| 6,675,807 | B2 | 1/2004 | Kittelsen et al. |
| 6,691,710 | B2 | 2/2004 | Kittelsen et al. |
| D496,154 | S | 9/2004 | Herman et al. |
| D496,498 | S | 9/2004 | Kittelsen et al. |
| 6,820,623 | B2 | 11/2004 | Cook |
| 6,837,246 | B1 | 1/2005 | DeLuke |
| 6,941,952 | B1 | 9/2005 | Rush, III |
| 7,059,332 | B2 | 6/2006 | Eli |
| 7,299,804 | B2 | 11/2007 | Kittelsen et al. |
| 7,798,149 | B2 | 9/2010 | Haduong |
| 7,890,193 | B2 | 2/2011 | Tingey |
| 7,950,394 | B2 | 5/2011 | Elkin |
| D641,478 | S | 7/2011 | Belvedere et al. |
| 8,074,658 | B2 | 12/2011 | Kittelsen et al. |
| 8,075,309 | B2 | 12/2011 | Li et al. |
| 8,113,206 | B2 | 2/2012 | Roettger et al. |
| 8,567,408 | B2 | 10/2013 | Roettger et al. |
| 8,667,972 | B2 | 3/2014 | Makkar et al. |
| 8,689,797 | B2 | 4/2014 | Elkin |
| 9,668,827 | B2 | 6/2017 | Roettger et al. |
| 10,328,225 | B2 | 6/2019 | Garner |
| 11,083,956 | B1 | 8/2021 | Varga |
| 11,129,746 | B2 | 9/2021 | Alvarez |
| 2002/0066454 | A1 | 6/2002 | Kittelsen et al. |
| 2002/0114694 | A1 | 10/2002 | Kittelsen et al. |
| 2002/0144687 | A1 | 10/2002 | Kittelsen et al. |
| 2002/0144688 | A1 | 10/2002 | Kittelsen et al. |
| 2002/0144689 | A1 | 10/2002 | Kittelsen et al. |
| 2002/0144690 | A1 | 10/2002 | Kittelsen et al. |
| 2002/0144691 | A1 | 10/2002 | Kittelsen et al. |
| 2002/0144692 | A1 | 10/2002 | Kittelsen et al. |
| 2002/0144693 | A1 | 10/2002 | Kittelsen et al. |
| 2002/0144695 | A1 | 10/2002 | Cook |
| 2003/0040679 | A1 | 2/2003 | Weber et al. |
| 2004/0094165 | A1 | 5/2004 | Cook |
| 2004/0107970 | A1 | 6/2004 | Kittelsen et al. |
| 2004/0181166 | A1 | 9/2004 | Williford et al. |
| 2004/0250817 | A1 | 12/2004 | Kittelsen et al. |
| 2005/0115571 | A1 | 6/2005 | Jacobs |
| 2005/0241646 | A1 | 11/2005 | Sotos et al. |
| 2005/0284489 | A1 | 12/2005 | Ambis |
| 2006/0078840 | A1 | 4/2006 | Robson |
| 2006/0289013 | A1 | 12/2006 | Keropian |
| 2007/0261701 | A1 | 11/2007 | Sanders |
| 2007/0289600 | A1* | 12/2007 | Li .................... A61F 5/566 128/860 |
| 2008/0099029 | A1* | 5/2008 | Lamberg ............ A61F 5/566 128/848 |
| 2008/0210244 | A1 | 9/2008 | Keropian |
| 2009/0130635 | A1 | 5/2009 | Tortorici |
| 2009/0191502 | A1 | 7/2009 | Cao et al. |
| 2009/0221884 | A1 | 9/2009 | Ryan |
| 2009/0308403 | A1 | 12/2009 | Roettger et al. |
| 2010/0147315 | A1 | 6/2010 | Chodorow |
| 2010/0252053 | A1 | 10/2010 | Garner et al. |
| 2010/0269836 | A1 | 10/2010 | Roettger et al. |
| 2011/0017221 | A1 | 1/2011 | Garner et al. |
| 2011/0039223 | A1 | 2/2011 | Li |
| 2011/0114100 | A1 | 5/2011 | Ramiro et al. |
| 2012/0165862 | A1 | 6/2012 | Mien |
| 2012/0305008 | A1 | 12/2012 | Garner et al. |
| 2013/0042876 | A1* | 2/2013 | Hermanson ........ A61M 15/00 128/848 |
| 2014/0026896 | A1 | 1/2014 | Roettger et al. |
| 2014/0080083 | A1 | 3/2014 | Mathieu |
| 2014/0090652 | A1* | 4/2014 | Hakimi ............... A61F 5/566 128/848 |
| 2015/0079530 | A1 | 3/2015 | Bergersen |
| 2015/0366636 | A1 | 12/2015 | Zampino |
| 2016/0367342 | A1 | 12/2016 | Alvarez |
| 2017/0020716 | A1 | 1/2017 | Hart et al. |
| 2018/0207022 | A1 | 7/2018 | Alvarez et al. |
| 2019/0262565 | A1 | 8/2019 | Garner |
| 2019/0374734 | A1 | 12/2019 | Garner |

FOREIGN PATENT DOCUMENTS

| | | |
|---|---|---|
| DE | 102004009883 | 9/2005 |
| FR | 2872406 | 3/2007 |
| GB | 2444588 | 3/2009 |
| GB | 2513902 A | 11/2014 |
| JP | 2006519656 A | 8/2006 |
| JP | 5008394 B2 | 8/2012 |
| JP | WO2014188517 A | 2/2017 |
| WO | 2009012243 | 1/2009 |
| WO | 2009128339 | 10/2009 |
| WO | 2009135210 | 11/2009 |
| WO | 2011153172 | 8/2011 |
| WO | 2011153173 | 8/2011 |
| WO | 2011153174 | 8/2011 |
| WO | 2011153175 | 8/2011 |

OTHER PUBLICATIONS

Fogel, Robert B., et al.; Within-Breath Control of Genioglossal Muscle Activation in Humans: Effect of Sleep-Wake State; The Journal of Physiology 550, 899-910; Aug. 1, 2003 (published online as of Jun. 13, 2003).

Garner, Dena P., The Effects of Mouthpiece Use on Gas Exchange Parameters During Steady-State in College-Aged Men and Woman, Journal of the American Dental Association 142(9), Sep. 2011.

Cheng, S., Movement of the Tongue During Normal Breathing in Awake, Healthy Humans, The Journal of Physiology 586, 4283-4294, Sep. 1, 2008 (published online as of Jul. 17, 2008).

Okeson; "Fundamentals of Occlusion and Temporomandibular Disorders" (The C. V. Mosby Company, St. Louis, 1985), p. 333-340.

Lucia; "Modem Gnathological Concepts—Updated" (Quintessence Publishing Co., Inc., Chicago, 1983), Chapters 2, 3, and 4 (pp. 29-63).

Shore; A Mandibular autorepositioning Appliance, JADA, vol. 75, Oct. 1967.

(56) References Cited

OTHER PUBLICATIONS

Shore, Nathan Allen, "Temporomandibular Joint Dysfunction and Occlusal Equilibration", J.B. Lippincott Compan, 1976 [Second Edition], Philadelphia, pp. 237-241.
Various Authors, Compednium of Continuing Education in Dentistry, 30(2) AEGIS Publications LLC, 2009.
D.P. Garner & E.J. McDivitt, Effects of Mouthpiece Use on Lactate and Cortisol Levels During and After 30 Minutes of Treadmill Running, Open Access Journal of Science and Technology, vol. 3, Agial Publishing House, 2015.
D.P. Garner, Effects of Various Mouthpieces on Respiratory Physiology During Steady-State Exercise in College-Aged Subjects, Sports Dentistry & Mouthgards, Academy of General Dentistry, Nov./Dec. 2015.
A.J. Miller, Oral and Pharyngeal Reflexes in the Mammalian Nervous System: Their Diverse Range in Complexity and Theh Pivotal Role of the Tongue, Crit. Rev. Oral Biol. Med., Inern'l & American Assoc. for Dental Research, 13(5): 409-425, 2002.
J.P. Saboisky, B.J. Luu, J.E. Butler, S.C. Gandevia, Effects of Tongue Position and Lung Volume on Voluntary Mximal Tongue Protrusion Force in Humands, Respiratory Physiology & Neurobiology, Elsevier, Dec. 4, 2014.
J.E. Schmidt, C.R. Carlson, A.R. Usery, A.S. Quevedo, Effects of Tongue Position on Mandibular Muscle Activity and Heart Rate Function, Oral Surg. Oral Med. Oral Path. Oral Radiol. Endod, Mosby Inc., 108:881-888, 2009.
D.P Garner, W.D. Dudgeon, E.J. Mcdivitt, the Effects of Mouthpiece Use On Cortisol Levels During an Intense Bout of Resistance Exercise, J. of Strength and Conditioning Research, National Strench & Conditioning Assoc., 25(10), 2011.
Murakami, S., Maeda, Y., Ghanem, A., Uchiyama, Y., & Kreilborg, S. Influence of Mouthguard on Temporomandibular Joint. Scand J Med Sports, 18, 591-595 (2008).
Pae, A., Yoo, R., Noh, K, Pake, J., & Kwon, K. the Effects of Mouthguards On the Athletic Ability of Professional Golfers. Dnen Traumatol, John Wiley & SON, 29, 47-51 (2013).
U.S. Appl. No. 17/484,592, filed Sep. 24, 2021 titled Method and Oral Appliance for Improving Air ntake and Reducing Bruxism.

* cited by examiner

SINGLE ARCH DENTAL DEVICE AND METHOD OF MANUFACTURE

BACKGROUND OF THE INVENTION

The present invention relates to a therapeutic oral appliance. More particularly, the present invention provides a single arch dental device that can be used for treating sleep and breathing disorders.

Many people suffer from sleep and breathing disorders, which are made up of complex muscle reflex responses. Obstructive Sleep Apnea (OSA), for example, is a serious sleep disorder which can cause a person to repeatedly stop and start breathing during sleep. OSA occurs when the muscles in the back of the throat relax too much to allow a normal volume of air to be inhaled. When a person's throat muscles relax their airway narrows or closes resulting in a reduced volume of air inhalation and lower oxygen intake. Such a reduction in oxygen may be inadequate for up to several minutes and may lower the oxygen level in the person's blood, thereby causing a buildup of carbon dioxide. The person's brain senses the impaired breathing and causes the person to wake and reopen the airway. Although such disruptions are necessary to restore a sufficient oxygen intake, they also impair the sufferer's ability to reach desired, restful phases of sleep. Such a lack of restful sleep can result in daytime fatigue, sleepiness, and cardiovascular complications related to increased blood pressure and strain on the cardiovascular system. Sufferers of OSA are particularly susceptible to grinding and gnashing their teeth during apnea episodes and the stress and fatigue resulting from disrupted sleep can lead to daytime grinding of the teeth.

Teeth grinding, known as bruxism, causes repeated stress and tension to the musculoskeletal structures of the jaw. As a person grinds his or her teeth, force is exerted in multiple directions, wearing down the teeth and causing muscle damage. If bruxism continues over a substantial period of time, the patient can suffer serious bone loss, cracked teeth, jaw muscle dysfunction, and other health problems. Some people also suffer from disorders affecting the temporomandibular joint (TMJ). The TMJ is located on each side of an individual's head in front of the ears, where the lower jaw meets the temporal bone. Often, the symptoms of bruxism and disorders affecting the TMJ are treated via the use of pain medications, muscle therapies, and nighttime oral appliances that protect the teeth and absorb shock. Treatment of the causes of bruxism can be difficult without further testing to determine whether the grinding is a result of anxiety and stress in the user's life, or if a breathing disorder such as sleep apnea is a factor. Sleep bruxism is another sleep disorder and people who suffer from sleep bruxism are more likely to have other sleep disorders, such as snoring and sleep apnea. In some people, bruxism can be frequent and severe enough to lead to jaw disorders, headaches, damaged teeth and other similar problems.

Devices have been disclosed in the known art that relate to therapeutic oral appliances. These include devices that have been patented and disclosed in patent application publications. However, the devices in the known art have several drawbacks. Many devices that are currently used to treat disorders that affect the TMJ, snoring, and obstructive breathing disorder symptoms function by requiring the interaction of both the mandibular and maxillary arch, as well as the relative positioning of the anterior and posterior aspects of the mandible. Other devices, such as a Continuous Positive Airway Pressure (CPAP) device provides a positive airway ventilator, which applies air pressure on a continuous basis to a user via a nosepiece or mask. Use of such a device can be difficult where the mask is an improper size and the user may have trouble getting accustomed to and tolerating the positive air pressure provided. The user may develop a dry and/or stuffy nose where the mask is not fitted properly. Leaks which may form between the mask and the user's skin may cause skin irritation or pressure sores. Some people get a feeling of claustrophobia when wearing a device such as a CPAP, and many people feel that traveling with such a device is difficult and wearing such a device is cumbersome, uncomfortable, and is generally too loud and noisy to attain peaceful rest.

SUMMARY OF THE INVENTION

In view of the foregoing disadvantages inherent in the known types of therapeutic oral appliances now known in the art, the present invention substantially diverges in design elements from the known art and it is clear that there is a need in the art for an improvement to existing therapeutic oral appliance devices. In this regard the present invention substantially fulfills these needs. The present invention provides even support to the TMJ, relieving the temporomandibular joint from excessive pressure caused from clenching and bruxism trauma. The present invention also provides protection to the wearer's teeth from fracture and excessive gum recession. The pocket of the present invention is configured to accept a wearer's tongue, such that the tongue can push the lower mandible forward past the upper anterior maxillary incisal edges. In this manner, minimal modifications compared to titratable equipment, such as a CPAP and upper and lower titratable devices, are needed to achieve proper airway dilation, thereby reducing or eliminating snoring.

The present invention provides a dental trough that includes a lingual surface, facial surface and an occlusal surface, and a pocket disposed on the posterior lingual surface of the trough, wherein the pocket is configured to receive an anterior and lateral border portion of a tongue of a wearer. The dental trough is molded to conform to the general shape of a wearer's lower teeth. The facial surface of the dental trough has an anterior facial surface and a posterior facial surface. The posterior facial surface of the dental trough is contoured to receive a facial surface of the wearer's teeth. The lingual surface of the dental trough has an anterior lingual surface and a posterior lingual surface. The anterior lingual surface of the dental trough is contoured to receive the lingual surface of the wearer's teeth. A pocket is carved out of the posterior lingual surface of the dental trough and provides a surface into which an anterior portion of a user's tongue rests.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1A:
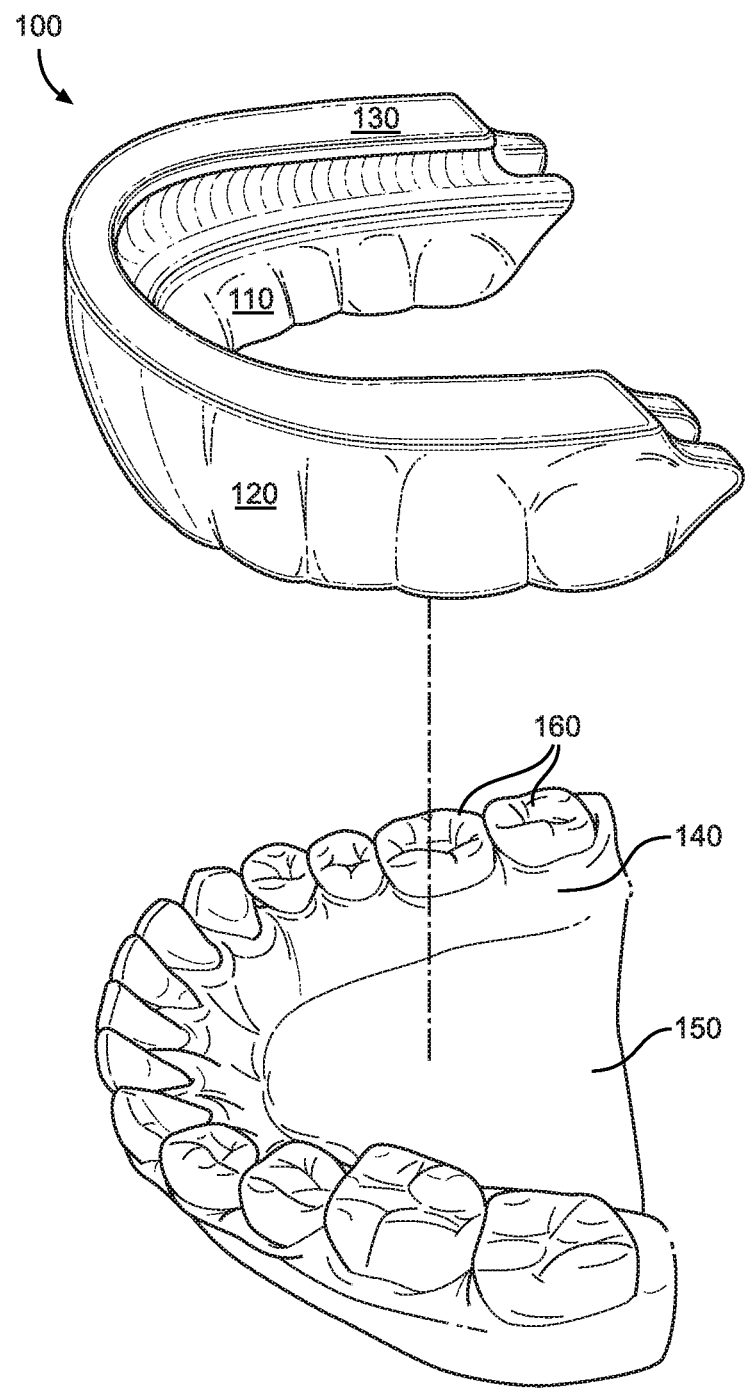
FIG. 1A shows a perspective view of an embodiment of the single arch dental device positioned above a lower set of teeth of a wearer.

Reference is made herein to the attached drawings. Like reference numerals are used throughout the drawings to depict like or similar elements of the single arch dental device. For the purposes of presenting a brief and clear description of the present invention, a preferred embodiment will be discussed as used for the single arch dental device. The figures are intended for representative purposes only and should not be considered to be limiting in any respect.

Figure 1B:
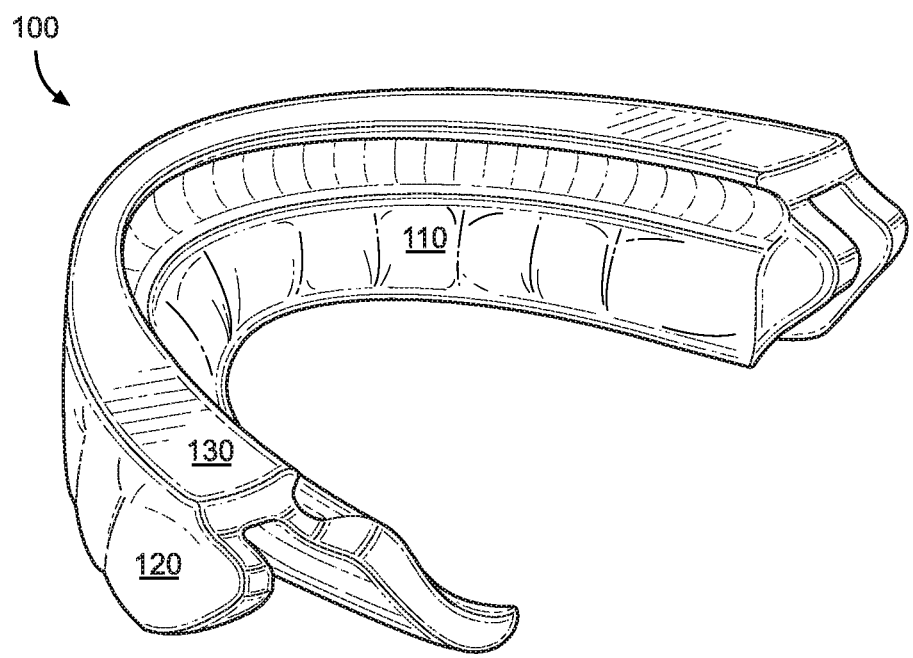
FIG. 1B shows a perspective view of an embodiment of the single arch dental device.

Referring now to FIGS. 1A and 1B, there are shown a perspective view of an embodiment of the single arch dental device positioned above a lower set of teeth of a wearer and a perspective view of an embodiment of the single arch dental device. The single arch dental device 100 comprises a dental trough, having a lingual surface 110, a facial surface 120 and an occlusal surface 130. In one embodiment, the single arch dental device has a minimum of 5 mm of vertical dimension. In various embodiments, an adjustment for a lower or higher vertical dimension can be accommodated per patient need. The structure of the single arch dental device 100 provides even support to the TMJ and relieves the temporal joint from excessive pressure caused from clenching and bruxism trauma, as further detailed below.

In various embodiments, the single arch dental device is comprised of acrylic and hard plastic materials, flexible and microwavable materials, dual laminate rubber, acrylic, ethylene vinyl acetate ("E.V.A."), or similar materials suitable for use in an oral appliance. Such materials provide protection to the teeth and gums from fracture and excessive gum recession. The flexible, E.V.A., acrylic, and hard plastic materials provide stronger materials which are able to withstand trauma associated with bruxism. Such materials are utilized by dental professionals and dental laboratories to provide a professional and custom fit to the wearer's teeth and anatomy. The microwavable materials allow a wearer to custom form and shape the single arch dental device 100, without having to utilize specialized dental professionals who may be costly both in time and price. Microwavable materials allow a user to form and shape the single arch dental device via heating the device in a microwave to soften the material, thereby allowing a wearer to mold the device to their teeth and anatomy. Other materials allow a wearer to boil the device in order to soften the material, and in a similar manner, allow the wearer to mold the device to their teeth and anatomy.

The lingual surface 110 is the exterior surface of the dental trough 100 that is the furthest interior residing surface, located closest to a wearer's tongue (as shown in FIG. 3, 300) when the single arch dental device is worn by the wearer. The lingual surface 110 extends past the wearer's gum line 140, and in some embodiments comprises a partial region that covers a portion of the floor of the mouth 150. Precise proportions of the partial region will vary according to the specific anatomy of the wearer. The facial surface 120 is the exterior surface of the dental trough 100 that is the furthest exterior-residing surface, located closest to the wearer's lips (as shown in FIG. 3, 310) when the single arch dental device 100 is worn by the wearer. Both the lingual surface 110 and the facial surface 120 extend along the entire dental trough. The facial surface 120 reaches down to the gum line 140 at each tooth, and terminates along a wearer's gum line 140, where the teeth meet the soft gum tissue, when the single arch dental device is worn. The occlusal surface 130 is the surface of the dental trough that connects the lingual surface 110 to the facial surface 120, located above the tops of the surfaces of the wearer's teeth 160 when the single arch dental device 100 is worn by the wearer.

Figure 2:
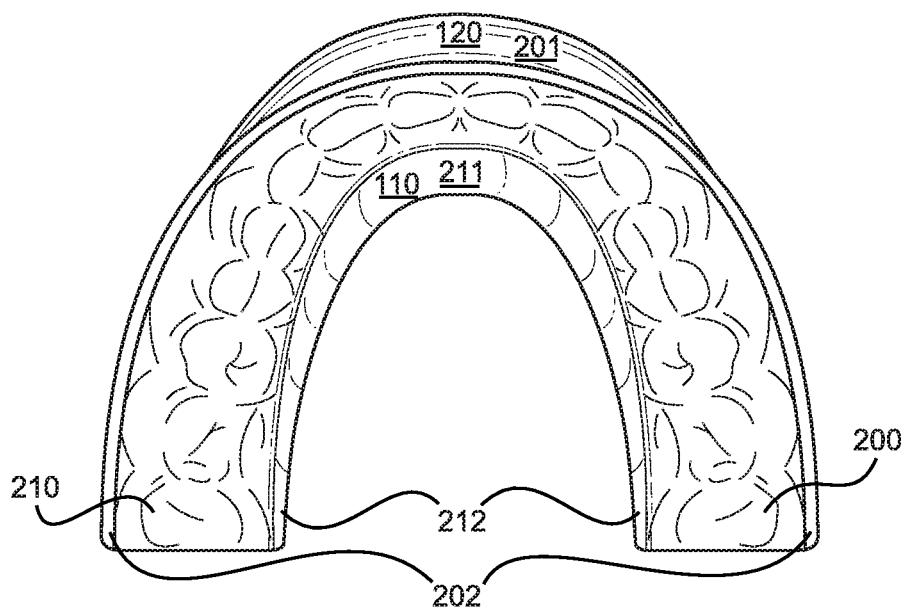
FIG. 2 shows an underside view of an embodiment of the single arch dental device.

Referring now to FIG. 2, there is shown an underside view of an embodiment of the single arch dental device. The dental trough is molded to conform to a wearer's teeth. In the shown embodiment, the dental trough extends from a right second molar position 200 on one side of the mouth to a left second molar 210 on the opposing side of the mouth. The facial surface 120 of the dental trough is further comprised of an anterior facial surface 201 and a posterior facial surface 202. The anterior facial surface 201 is that external surface of the dental trough that resides between the facial surface of the wearer's teeth and the lips of the wearer. The posterior facial surface 202 of the dental trough is an interior surface of the trough contoured to receive a facial surface of the wearer's teeth. Similarly, the lingual surface 110 of the dental trough is further comprised of an anterior lingual surface 211 and a posterior lingual surface 212. The anterior lingual surface 211 of the dental trough is an interior surface of the dental trough contoured to receive a lingual surface of the wearer's teeth. The posterior lingual surface 212 of the dental trough is that external surface of the dental trough that resides between the lingual surface of the wearer's teeth and an interior volume of the wearer's mouth. By operation of the contoured fit of the anterior lingual surface 211 and the anterior facial surface 201 of the dental trough around the wearer's teeth, the single arch dental device is configured to snugly fit over the wearer's lower teeth via friction. In such a manner, the dental trough mimics the contours of the wearer's teeth and the dental trough is prevented from sliding when worn by the wearer, thereby providing stability.

Figure 3A:
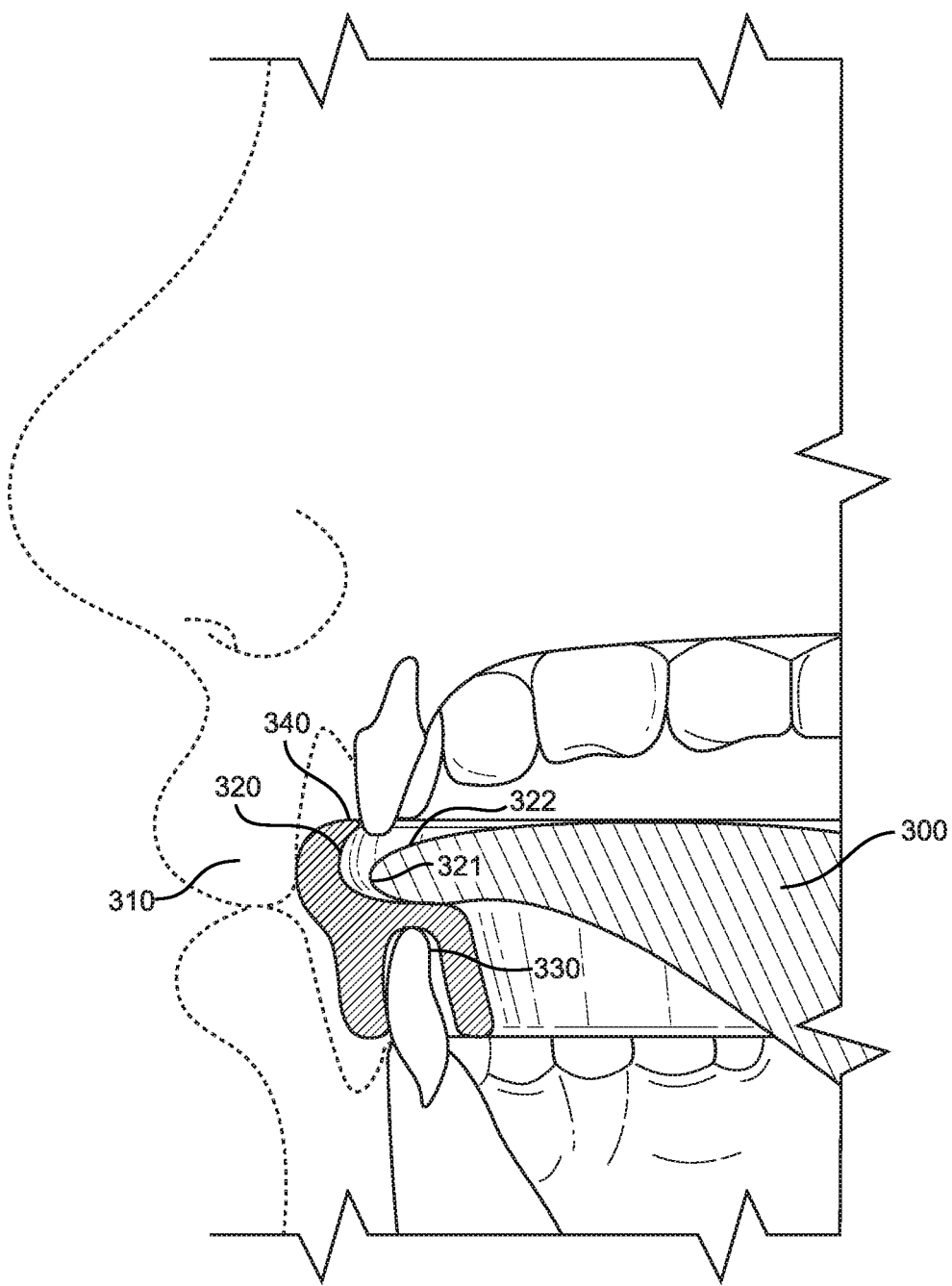
FIG. 3A shows a side cross-sectional view of an embodiment of the single arch dental device, in use by the wearer.

Referring now to FIG. 3A, there is shown a side cross-sectional view of an embodiment of the single arch dental device, in use by the wearer. The dental trough includes a pocket 320 disposed on the posterior lingual surface. In one embodiment, the dental trough includes a build-up of acrylic on top of the occlusal surface of up to 5 mm disposed above a clinical crown 330 of the wearer's teeth. In various embodiments, a build-up of acrylic on top of the occlusal surface is within +/−5 mm in order to accommodate for a larger or smaller build-up per the wearer's needs. In further embodiments, a build-up of acrylic on top of the occlusal surface of +/−5 mm is added or subtracted in order to further customize the device. In the shown embodiment, the pocket 320 is carved out of acrylic and is contoured to follow a curve 321 of the wearer's tongue 300. The pocket 320 is continuously disposed on top of the occlusal surfaces. In one embodiment, the pocket 320 begins at a right first molar and ends at a left first molar. In another embodiment, the pocket 320 begins at a right second molar and terminates at a left second molar. In other embodiments, the pocket 320 begins at a selection of a right first or second molar and terminates at a selection of a left first or second molar. In various embodiments, the pocket 320 has a gradually increased slope around the lower dental arch and fills a +/-5 mm vertical space. In such a manner, the pocket 320 of the single arch dental device is configured to receive an anterior portion 322 of a tongue 300 of a wearer, such that the tongue 300 can rest within the pocket 320.

In the shown embodiment, the pocket further comprises an overhang 340. The overhang 340 continues the contour of the pocket 20 and forms a concave element of the pocket 320. The concave curve of the pocket 320 surrounds the anterior portion 322 of a user's tongue 300 further securing the tongue 300 in position. The overhang 340 helps to ensure that the tongue 300 does not slip out of the pocket 320 by enclosing the tongue 300 on three surfaces; the top, bottom, and tip thereof. The tongue 300 rests in the pocket 320 by its own natural muscle force and nerve reflex. It is contemplated by this disclosure that a variety of different sizes of pocket 320 are available to conform to the unique and shape of the size wearer's tongue 300.

The pocket 320 provides an open space to facilitate the tongue 300 to fit into and push a lower mandible of the wearer forward past an upper anterior maxillary incisal edge. In such a manner, the single arch dental device does not require many modifications or titration equipment in order to achieve proper airway dilation to reduce or eliminate snoring, similar to the benefits available of using of a CPAP machine. When the tongue 300 is received in the pocket 320, the tongue 300 will naturally push forward within its natural nerve and muscle reflex for an automatic titration to occur. This automatic titration does not require any additional suction, therefore providing a benefit of the present device over other devices known in the art.

Figure 3B:
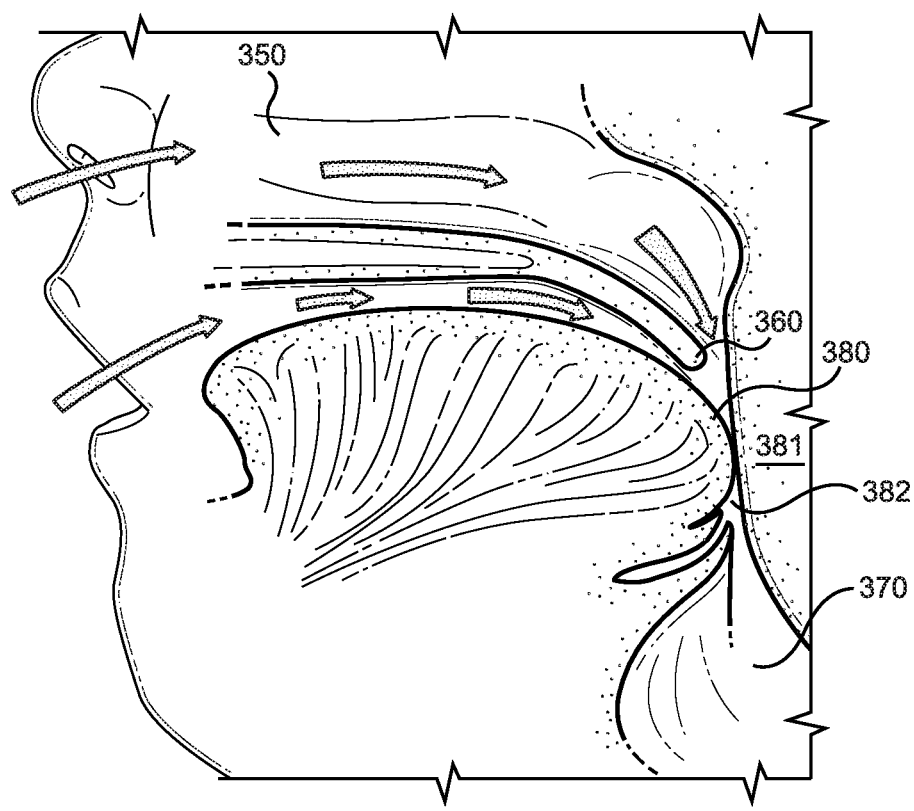
FIG. 3B shows a side cross-sectional view of an individual suffering from Obstructive Sleep Apnea.
Figure 3C:
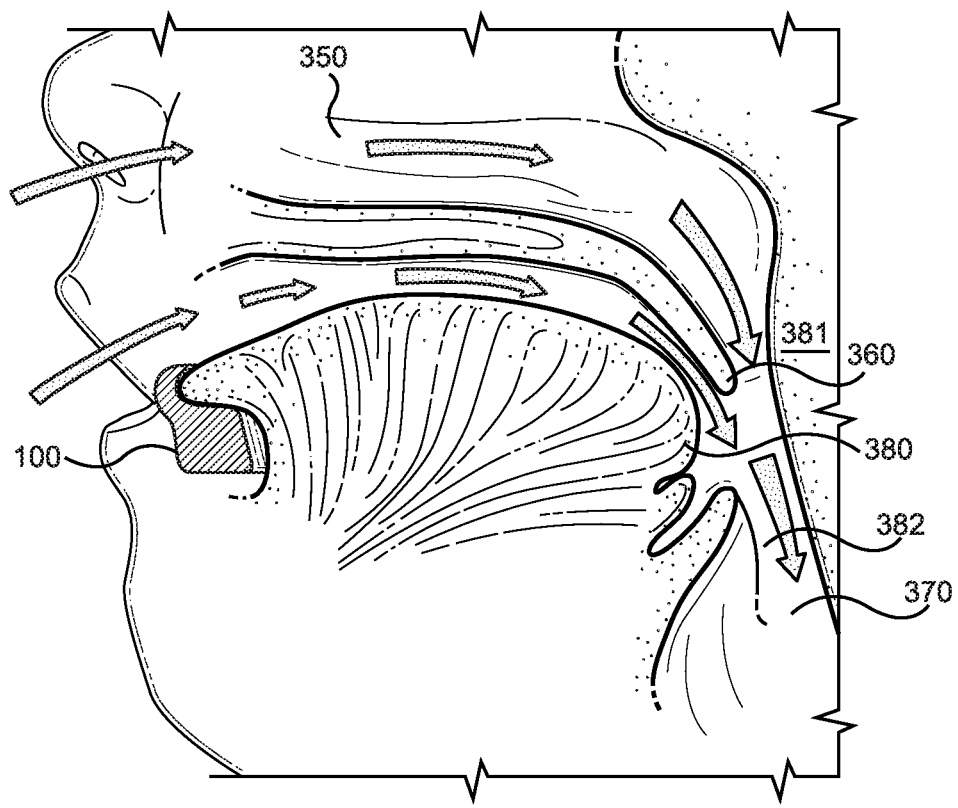
FIG. 3C shows a side cross-sectional view of an embodiment of the single arch dental device, in use treating an individual suffering from Obstructive Sleep Apnea.

Referring now to FIGS. 3B and 3C there are shown a side cross-sectional view of an individual suffering from Obstructive Sleep Apnea and a side cross-sectional view of an embodiment of the single arch dental device, in use treating an individual suffering from Obstructive Sleep Apnea. As described earlier, an individual breathes in through their nose and mouth. The flow of air passes through the nasal cavity 350 or mouth, past the uvula 360, and proceeds down through the throat 370. In an individual suffering from obstructive sleep apnea, the back of their tongue 380 rests against a back surface 381 of an airway 382 leading into the throat 370. By utilization of the single arch dental device 100, the individual's tongue pushes forward within its natural nerve and muscle reflex resulting in the back of their tongue 380 moving away from the back surface 381 of the airway 382 resulting in automatic titration. This reflex results in the airway 382 being maintained in an open position, thereby allowing the flow of air to continue from the nose and mouth, down the airway 382 into the throat 370.

Figure 4:
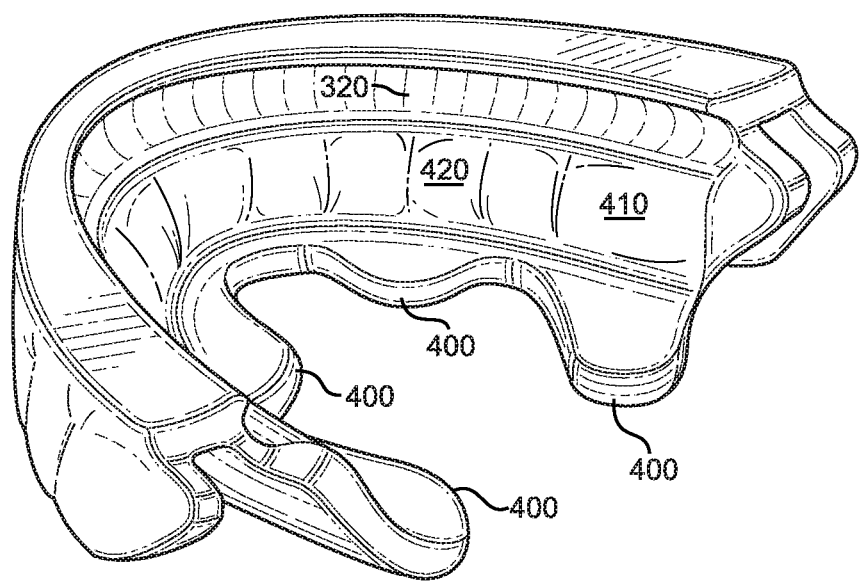
FIG. 4 shows a perspective view of the single arch dental device, with a focus on the lateral members.

Referring now to FIG. 4, there is shown a perspective view of the single arch dental device, with a focus on the lateral members. In one embodiment, at least one pair of lateral members 400 are disposed on laterally opposing sides of a portion of the posterior lingual surface 410. The lateral members 400 are positioned to interact with posterior margins of a dorsum of the wearer's tongue. The lateral members 400 serve to guide the wearer's tongue into the pocket 320 formed in parallel with the floor of the wearer's mouth, and along the contours of the single arch dental device such that the anterior and lateral border portion of the tongue 322 of the user is guided into the pocket 320. In such a manner, the wearer's tongue is positioned to push forward with its natural nerve and muscle reflex for automatic titration. Titration is the process of obtaining a pressure required to resolve apnea episodes. CPAP titration the pressure is trialed up and down until pressure and settings are determined to resolve apnea episodes. Automatic titration is desirable over CPAP titration because the present device utilizes the natural nerve and muscle reflex to obtain the desired pressure. In another embodiment, at least one pair of lateral members 400 are disposed on laterally opposing sides of a portion of the anterior lingual surface 420. In various embodiments, a selection of anterior and posterior positions is utilized to selectively guide the user's tongue into position in the pocket 320.

Figure 5:
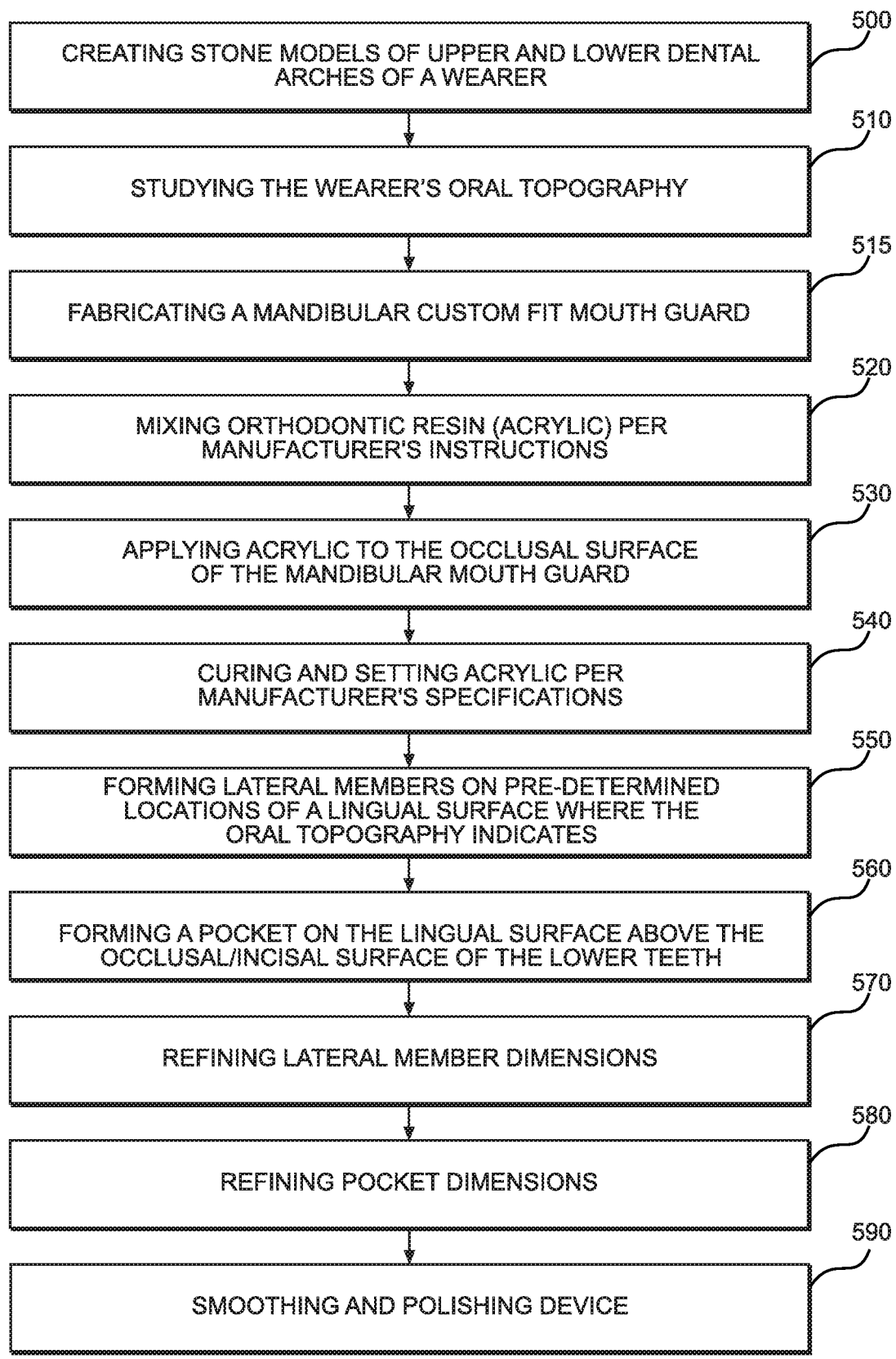
FIG. 5 shows a flowchart of a method of formation of the single arch dental device utilizing plastic and acrylic.

Referring now to FIG. 5, there is shown a flowchart of a method of formation of the single arch dental device utilizing plastic and acrylic. The first step in creating a single arch dental device comprising Erkodent® or hard plastic and acrylic is creating a stone model of the upper and lower dental arches of a wearer 500. The single arch dental device is custom made to friction fit snugly over the wearer's teeth. Studying the wearer's oral topography 510 enables an individual crafting the single arch dental device to plan out the location of various features such as locations for lateral protuberances and the size and depth of the pocket. Fabricating a mandibular custom fit mouth guard 515 is accomplished by mixing an orthodontic resin 520 per the manufacturer's instructions. Applying acrylic to the occlusal surface of the mandibular mouth guard 530 provides a base onto which the single arch dental device can be fine-tuned and provides material to the individual crafting the single arch dental device to be utilized in forming and shaping the pocket. In one embodiment, a strong and durable hard plastic of 2 mm is used. In another embodiment, a strong and durable hard plastic of 3 mm is used. After the hard plastic is added and shaped to a dental arch, adding +/-5 mm of acrylic to occlusal surface allows a pocket to be formed therefrom. In one embodiment, additional acrylic is added to the occlusal surface to form a vertical support of over 5 mm, in order to further customize the pocket to the anatomy of the wearer. Curing and setting the acrylic per the manufacturer's instructions 540 stabilizes the device.

Lateral members are formed on pre-determined locations of a lingual surface where the oral topography indicates 550. A pocket is formed on the lingual surface above the occlusal/incisal surface of the lower teeth 560. Such a pocket results in a defined area in which the wearer's tongue can push and rest. The acrylic is then set, and refinements to the lateral member dimensions 570 as well as pocket dimensions 580 enable the individual crafting the single arch dental device to fully customize the size and shape of the device, pocket, and lateral members to the unique contours of the wearer's teeth, gums, and tongue. Smoothing and polishing the device 590 provides a non-abrasive surface that does not irritate the wearer when in use.

Figure 6:
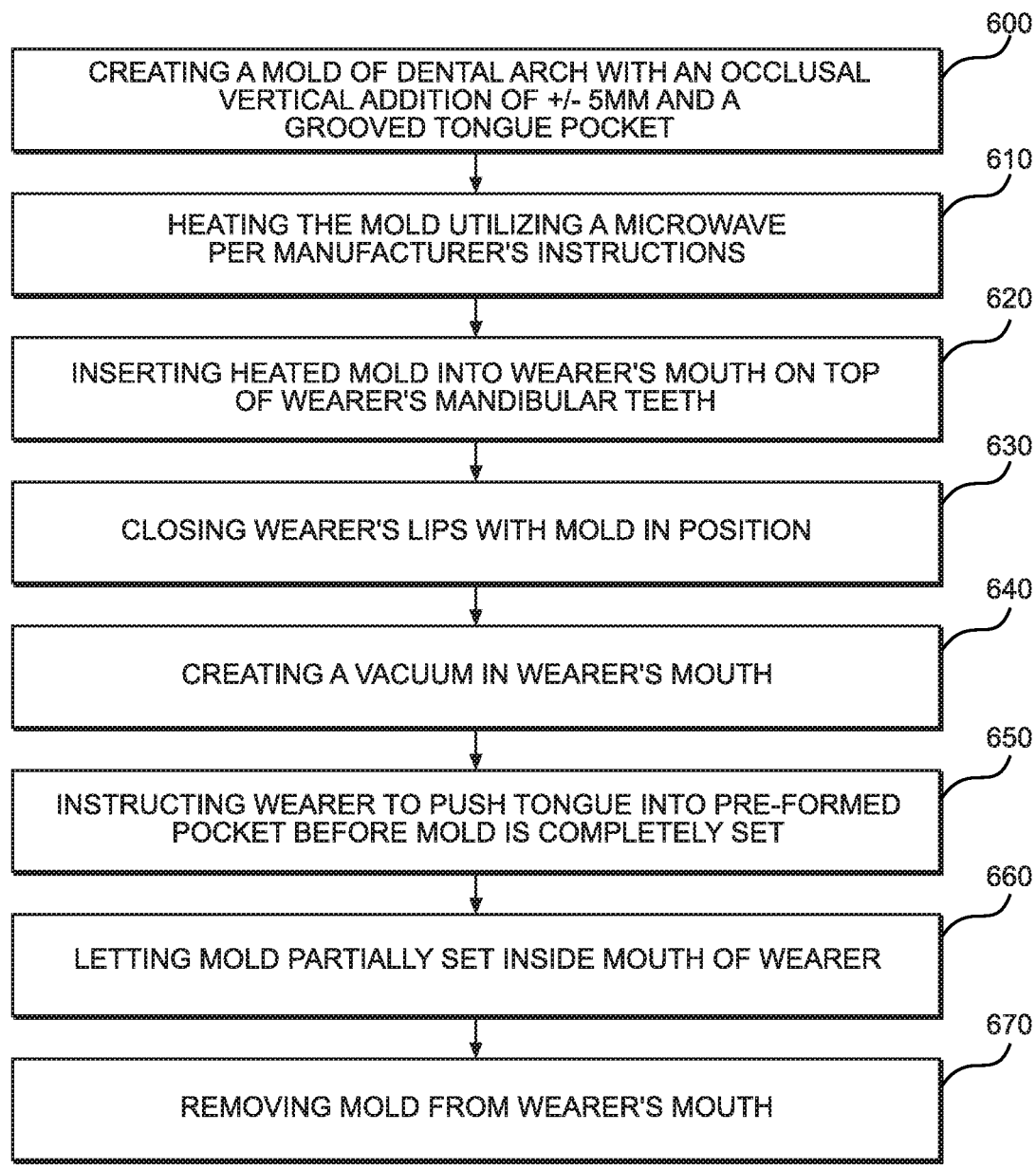
FIG. 6 shows a flowchart of a method of formation of the single arch dental device utilizing microwavable material.

Referring now to FIG. 6, there is shown a flowchart of a method of formation of the single arch dental device utilizing microwavable material. In various embodiments, microwavable material is used to form a general mold of a dental arch with an occlusal vertical addition of +/-5 millimeters on an occlusal surface as well as a generalized grooved tongue pocket 600. In various embodiments, the general mold is a variety of sizes and is categorized into small, medium, large, and extra-large molds. Heating the mold utilizing a microwave per the manufacturer's specifications 610 enables the mold to be malleable and customized to an individual wearer. Inserting the heated mold into the wearer's mouth on top of the wearer's mandibular teeth 620 aligns the mold in a position to create a custom fit of the mold onto the wearer's lower teeth. Closing the wearer's lips with the mold in position 630 and creating a vacuum in the wearer's mouth 640 allows the mold to flow over the wearer's teeth and create such a custom fit. Instructing the wearer to push their tongue into the pre-formed pocket before the mold is completely set 650 customizes the fit of the pocket to the shape and size of the wearer's tongue. Letting the mold partially set inside the mouth of the wearer 660 allows the mold to solidify and retain the size and shape of the wearer's teeth and tongue. Removing the mold from the wearer's mouth 670 allows the mold to finally set and harden while retaining the size and shape of the wearer's teeth and tongue.

Figure 7:
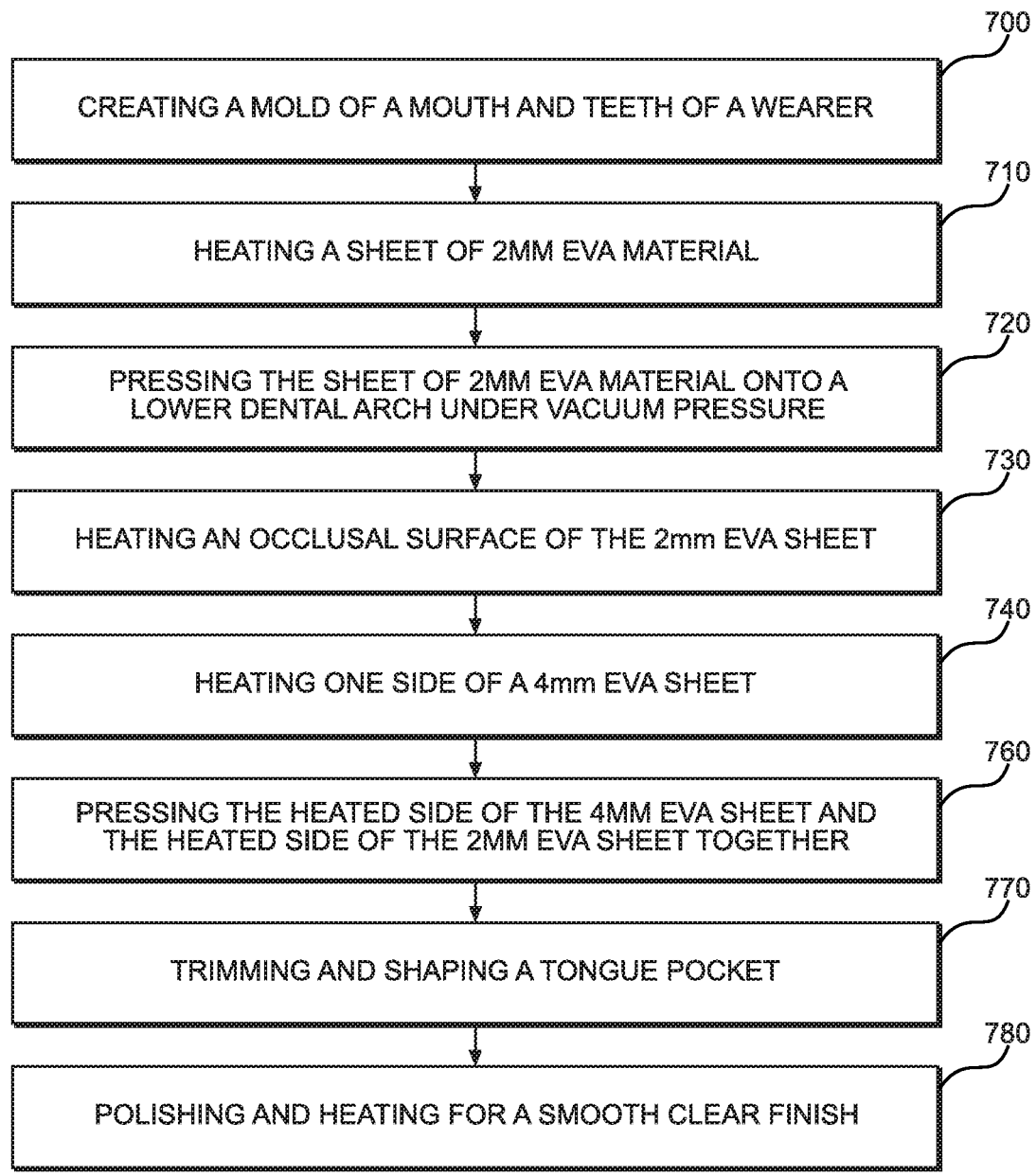
FIG. 7 shows a flowchart of a method of formation of the single arch dental device utilizing ethylene vinyl acetate ("E.V.A.") material.

Referring now to FIG. 7, there is shown a flowchart of a method of formation of the single arch dental device utilizing E.V.A. material. The first step in creating a single arch dental device comprising E.V.A. materials is creating a mold of a teeth and gums of a wearer 700. The single arch dental device is custom made to friction fit snugly over the wearer's teeth. A sheet of 2-millimeter E.V.A. material is heated 710 and pressed onto a lower dental arch under vacuum pressure 720. An occlusal surface of the 2-millimeter E.V.A. sheet is heated 730 as is one side of a sheet of 4-millimeter E.V.A. material 740. The heated side of the 4-millimeter E.V.A. sheet and the heated side of the 2-millimeter E.V.A. sheet is pressed together 760. The E.V.A. sheets are trimmed and shaped to form a desired tongue pocket 770. The resulting device is polished and heated for a smooth and clear finish 780.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:
1. A single arch dental device, comprising:
a dental trough, having a lingual surface, a facial surface and an occlusal surface, the dental trough molded and adapted to conform to a wearer's teeth;
the facial surface having an anterior facial surface and a posterior facial surface; the posterior facial surface contoured and adapted to receive a facial surface of the wearer's teeth;
the lingual surface having an anterior lingual surface and a posterior lingual surface;
the anterior lingual surface contoured and adapted to receive a lingual surface of the wearer's teeth;
a pocket disposed on the posterior lingual surface;
wherein the pocket is configured to receive an anterior portion of a tongue of the wearer;
at least one pair of lateral members disposed on laterally opposing sides of a portion of the posterior lingual surface;
the at least one pair of lateral members adapted to interact with posterior margins of a dorsum of the wearer's tongue.

2. The single arch dental device of claim 1, wherein each of the lingual surface, the facial surface, and the occlusal surface has a thickness of 5 mm or less.

3. The single arch dental device of claim 1, wherein the pocket has a a space measured in vertical direction of 5 mm or less.

4. The single arch dental device of claim 1, wherein the pocket is contoured and adapted to follow a curve of the wearer's tongue.

5. The single arch dental device of claim 1, wherein the pocket is adapted to be above a clinical crown of the wearer's teeth.

6. The single arch dental device of claim 1, wherein the dental trough is comprised of acrylic and hard plastic materials.

7. The single arch dental device of claim 1, wherein the dental trough is comprised of a flexible material capable of being heated in a microwave.

8. The single arch dental device of claim 1, wherein the dental trough is comprised of dual laminate rubber and acrylic.

9. The single arch dental device of claim 1, wherein the dental trough is comprised of E.V.A. flexible material.

* * * * *